(12) United States Patent
Stimson et al.

(10) Patent No.: US 9,469,556 B2
(45) Date of Patent: Oct. 18, 2016

(54) BALLAST WATER TREATMENT SYSTEM

(75) Inventors: William Stimson, Glasgow (GB); Peilin Zhou, Glasgow (GB); Dracos Vassalos, Glasgow (GB); Atilla Incecik, Glasgow (GB)

(73) Assignee: University of Strathclyde, Glasgow (GB)

( * ) Notice: Subject to any disclaimer, the term of this patent is extended or adjusted under 35 U.S.C. 154(b) by 1208 days.

(21) Appl. No.: 13/146,821

(22) PCT Filed: Jan. 29, 2010

(86) PCT No.: PCT/GB2010/000134
§ 371 (c)(1),
(2), (4) Date: Jan. 17, 2012

(87) PCT Pub. No.: WO2010/086604
PCT Pub. Date: Aug. 5, 2010

(65) Prior Publication Data
US 2012/0115723 A1 May 10, 2012

(30) Foreign Application Priority Data
Jan. 29, 2009 (GB) .................................. 0901434.1

(51) Int. Cl.
| | |
|---|---|
| *A01N 33/12* | (2006.01) |
| *A01N 43/16* | (2006.01) |
| *A01N 57/20* | (2006.01) |
| *C02F 1/50* | (2006.01) |
| C02F 103/00 | (2006.01) |
| C02F 103/10 | (2006.01) |

(52) U.S. Cl.
CPC .................. *C02F 1/50* (2013.01); *A01N 33/12* (2013.01); *A01N 43/16* (2013.01); *A01N 57/20* (2013.01); *C02F 2103/008* (2013.01); *C02F 2103/10* (2013.01)

(58) Field of Classification Search
CPC ...... A01N 33/12; A01N 43/16; A01N 57/20; C02F 1/50; C02F 2103/008; C02F 2103/10
See application file for complete search history.

(56) References Cited

U.S. PATENT DOCUMENTS

| | | | | |
|---|---|---|---|---|
| 3,083,089 | A | * | 3/1963 | Renner .......................... 504/126 |
| 3,644,238 | A | * | 2/1972 | Smith ...................... C10L 1/006 106/18.31 |
| 4,087,597 | A | * | 5/1978 | Hafeli .................. C07D 219/08 106/18.29 |
| 4,992,531 | A | | 2/1991 | Patroni et al. |
| 5,128,050 | A | | 7/1992 | Gill |
| 5,158,596 | A | | 10/1992 | Sherba et al. |
| 5,441,743 | A | * | 8/1995 | McGinniss .......... C09D 5/1625 424/405 |
| 5,705,269 | A | | 1/1998 | Pimenov et al. |
| 5,932,112 | A | | 8/1999 | Browning, Jr. |
| 6,168,794 | B1 | * | 1/2001 | Reusser et al. ............... 424/769 |
| 6,340,468 | B1 | | 1/2002 | Cutler et al. |
| 2003/0012804 | A1 | | 1/2003 | Cutler et al. |
| 2003/0029811 | A1 | | 2/2003 | Russell |
| 2003/0121464 | A1 | | 7/2003 | O'Reilly et al. |
| 2004/0129645 | A1 | | 7/2004 | Perlich et al. |
| 2006/0003894 | A1 | | 1/2006 | Cutler et al. |
| 2007/0254854 | A1 | * | 11/2007 | Magallon et al. ............ 514/150 |
| 2008/0227856 | A1 | * | 9/2008 | Melker ........................ 514/470 |
| 2008/0317700 | A1 | * | 12/2008 | Neckers ................. A01N 57/20 424/78.09 |

FOREIGN PATENT DOCUMENTS

| | | |
|---|---|---|
| CN | 10 0998333 A | 7/2007 |
| EP | 1 717 205 A1 | 11/2006 |
| GB | 112149 A | 1/1918 |
| JP | S64-47389 A | 2/1989 |
| JP | 1-249199 A | 10/1989 |
| JP | H04-178310 A | 6/1992 |
| JP | H05-92903 A | 4/1993 |
| JP | H07-509236 A | 10/1995 |
| JP | H07-509263 A | 10/1995 |
| JP | 2004-000364 A | 1/2004 |
| WO | WO 93/23474 A1 | 11/1993 |
| WO | WO 94/02022 A1 | 2/1994 |
| WO | WO 01/60971 A2 | 8/2001 |
| WO | WO 02/082907 A1 | 10/2002 |

(Continued)

OTHER PUBLICATIONS

Daniel Y. C. Fung and Richard D. Miller, "Effect of Dyes on Bacterial Growth", Applied Microbiology, May 1973, 25(5):793-799.*
E. F. J. Duynstee and Ernest Grunwald, "Organic Reactions Occurring in or on Micelles. I. Reaction Rate Studies of the Alkaline Fading of Triphenylmethane Dyes and Sulfonphthalein Indicators in the Presence of Detergent Salts", Journal of the American Chemical Society, 1959, 81 (17), pp. 4540-4542.*
Yoshihiro Taniguchi and Akira Iguchi, "Effect of pressure on the rate of alkaline fading of triphenylmethane dyes in cationic micelles", Journal of the American Chemical Society, 1983, 105 (23), pp. 6782-6786.*

(Continued)

*Primary Examiner* — John Pak
*Assistant Examiner* — Nathan W Schlientz
(74) *Attorney, Agent, or Firm* — Alston & Bird LLP

(57) ABSTRACT

A composition for treating waters, e.g. ballast water or injection water for oil recovery, to kill in-situ aquatic invasive species comprises at least one biocide capable of killing both animal and plant micro-organisms. The at least one biocide preferably comprises Brilliant Green, Gentian Violet, and/or erythrosine, and a wetting agent or detergent-like compound such as CTAB or CTAC. The invention also relates to a system for treating ballast water in situ comprising means for injecting a composition for treating ballast water; means for measuring the flow rate or amount of ballast water to be treated; means for controlling the dosing of the composition; and means for storing or receiving the composition. The invention also relates to a method of detecting viable aquatic organisms in ballast water in situ comprising detecting metabolism in viable micro-organisms in ballast water and, therefore, measuring the efficacy of any treatment.

17 Claims, 9 Drawing Sheets

(56) References Cited

FOREIGN PATENT DOCUMENTS

WO  WO 2007/020353 A2  2/2007
WO  WO 2007/116051 A1  10/2007

OTHER PUBLICATIONS

Mercedes Valiente and Elvira Rodenas, "Influence of Cetyltrimethylammonium Bromide/1-Hexanol and Cetyltrimethylammonium Bromide/1-Octanol Mixed Micelles on the Basic Hydrolysis of Crystal Violet. Different Theoretical Approaches", Langmuir 1990, 6(4), 775-782.*

Mercedes Valiente and Elvira Rodenas, "Reverse Cetyltrlmethylammonium Bromide Micelles in Alkanols: Influence on the Basic Hydrolysis of Crystal Violet", The Journal of Physical Chemistry 1991, 95(8), 3368-3370.*

Office Action for Japanese Application No. 2011-546949 dated Mar. 4, 2014, 4 pages.

International Search Report for Application No. PCT/GB2010/000134 dated Feb. 29, 2012.

Search Report for GB 0901434.1 dated Mar. 30, 2009.

International Preliminary Report on Patentability and Written Opinion from International Application No. PCT/GB2010/000134, dated Feb. 28, 2012.

* cited by examiner

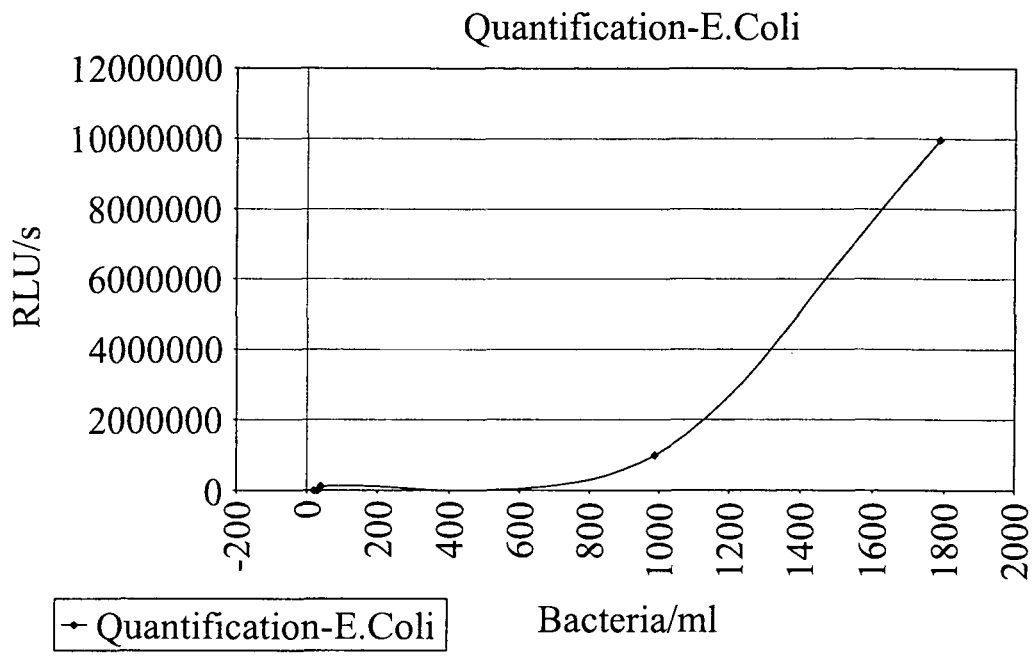
Fig 2.1
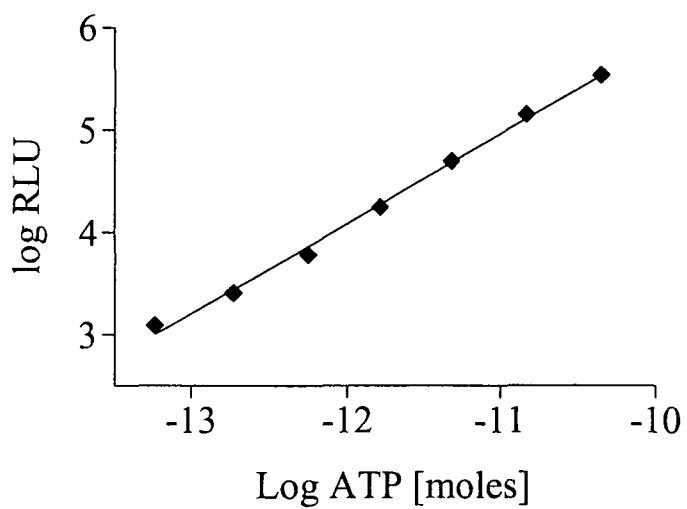
Fig 2.2

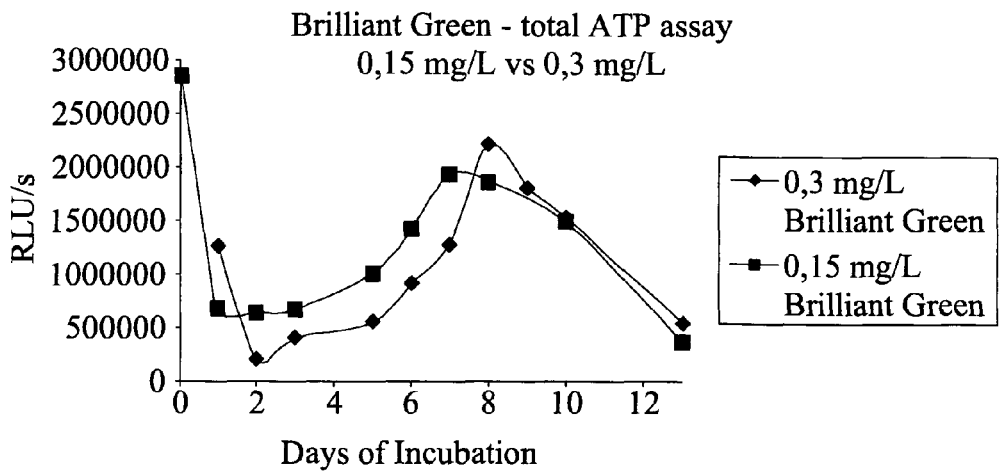
Fig 3.1
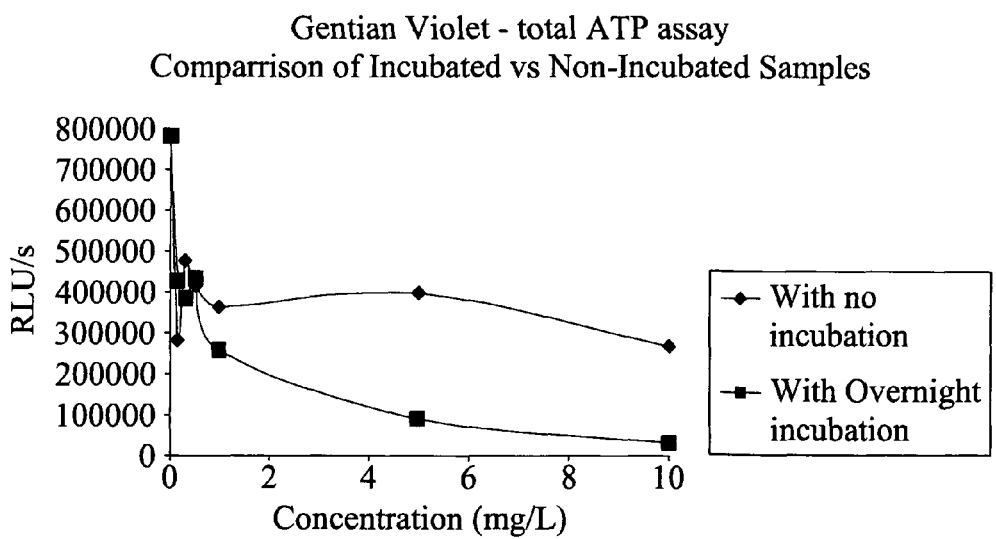
Fig 3.2

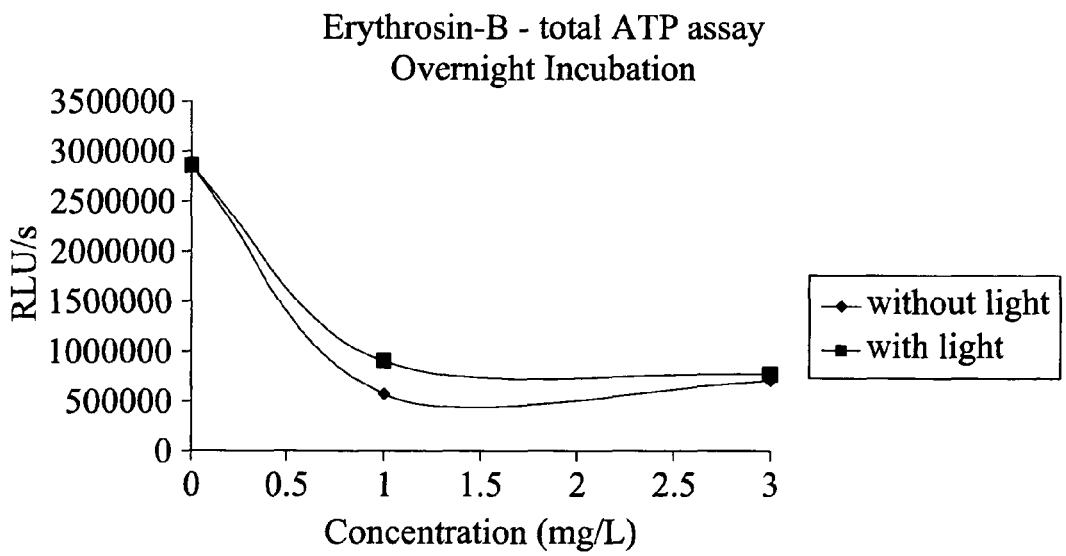
Fig 3.3
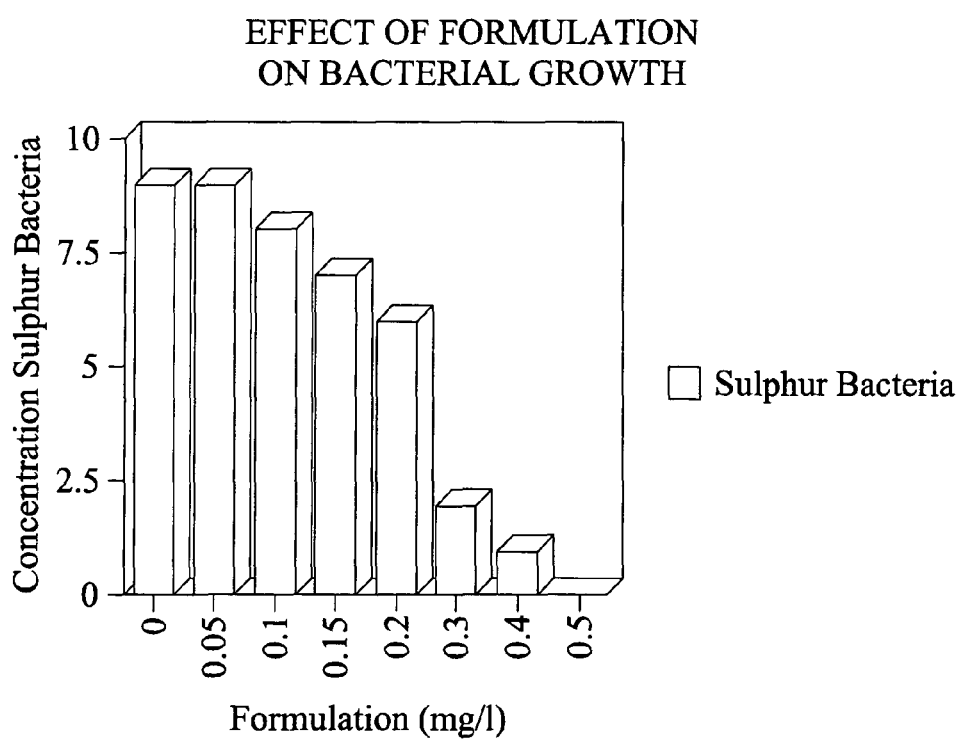
Fig 3.4

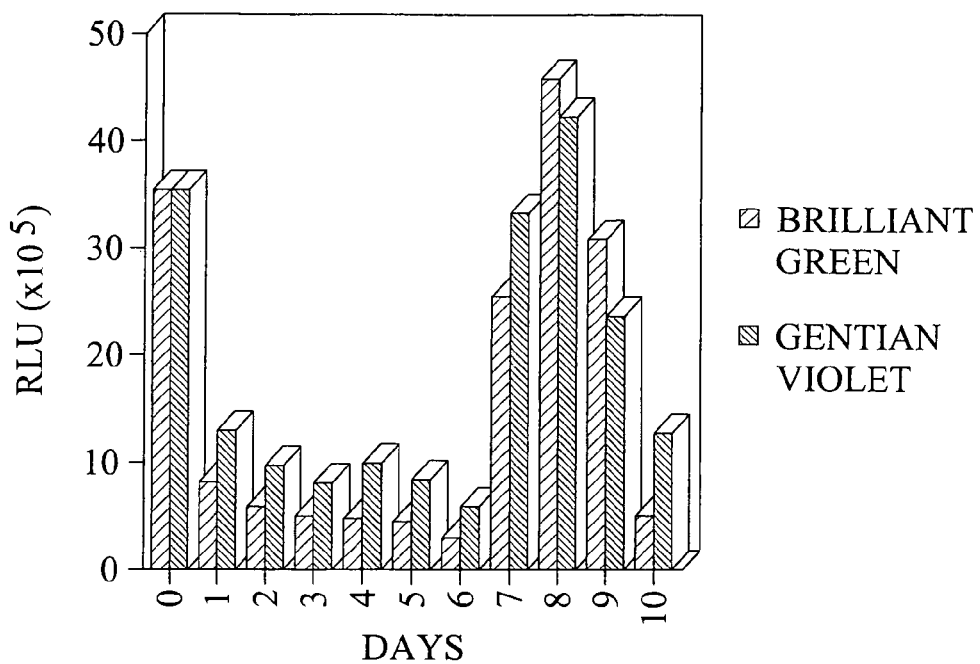
Fig 4.1
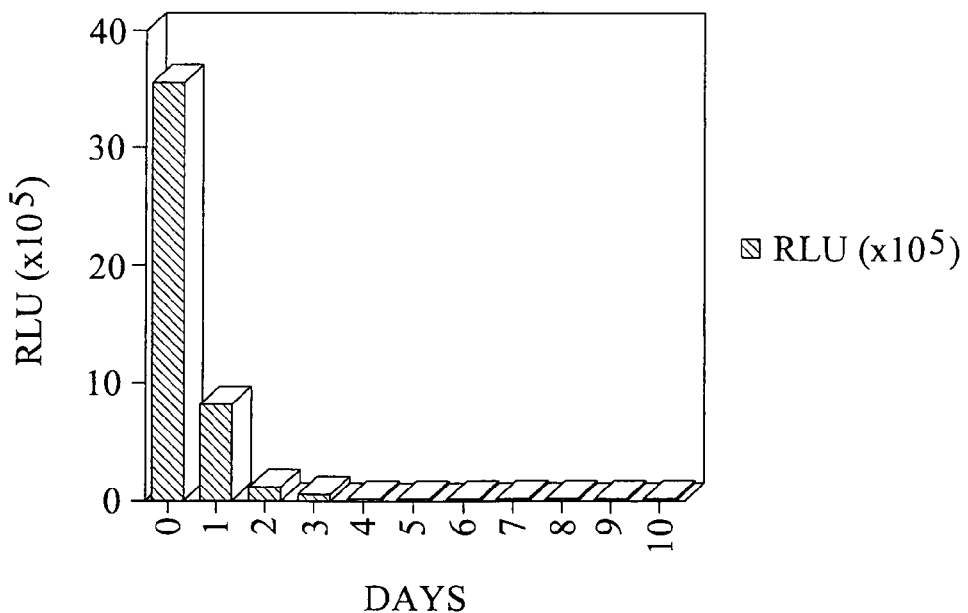
Fig 4.2

| Concentration Number | CTAB Concentration (mg/L) | BG Concentration (mg/L) |
|---|---|---|
| 1 | 1 | 0.5 |
| 2 | 0.8 | 0.4 |
| 3 | 0.6 | 0.3 |
| 4 | 0.4 | 0.2 |
| 5 | 0.2 | 0.1 |
| 6 | 1 | 0.1 |
| 7 | 0.8 | 0.2 |
| 8 | 0.4 | 0.4 |
| 9 | 0.2 | 0.5 |
| 10 | 0.5 | 0.5 |
| 11 | 0.3 | 0.3 |
| 12 | 0.2 | 0.2 |
| 13 | 0.1 | 0.1 |
| 14 | 0.5 | 0.1 |
| 15 | 0.2 | 0.4 |
| 16 | 0.1 | 0.5 |
| 17 | CONTROL (0) | CONTROL (0) |
Fig 5.1
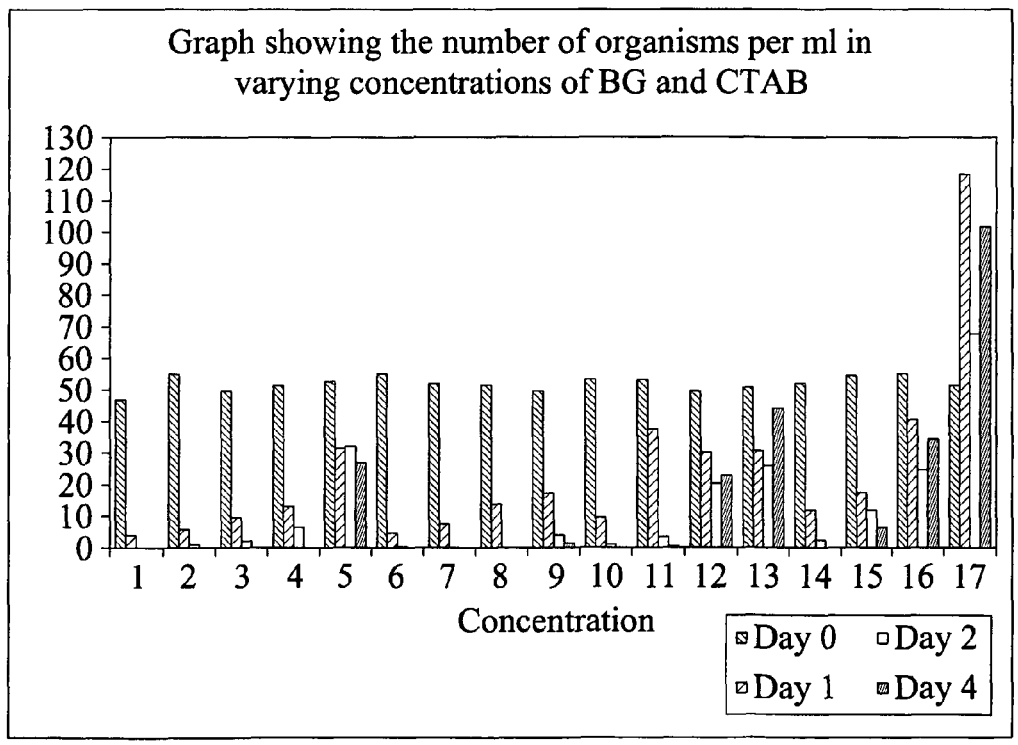
Fig 5.2

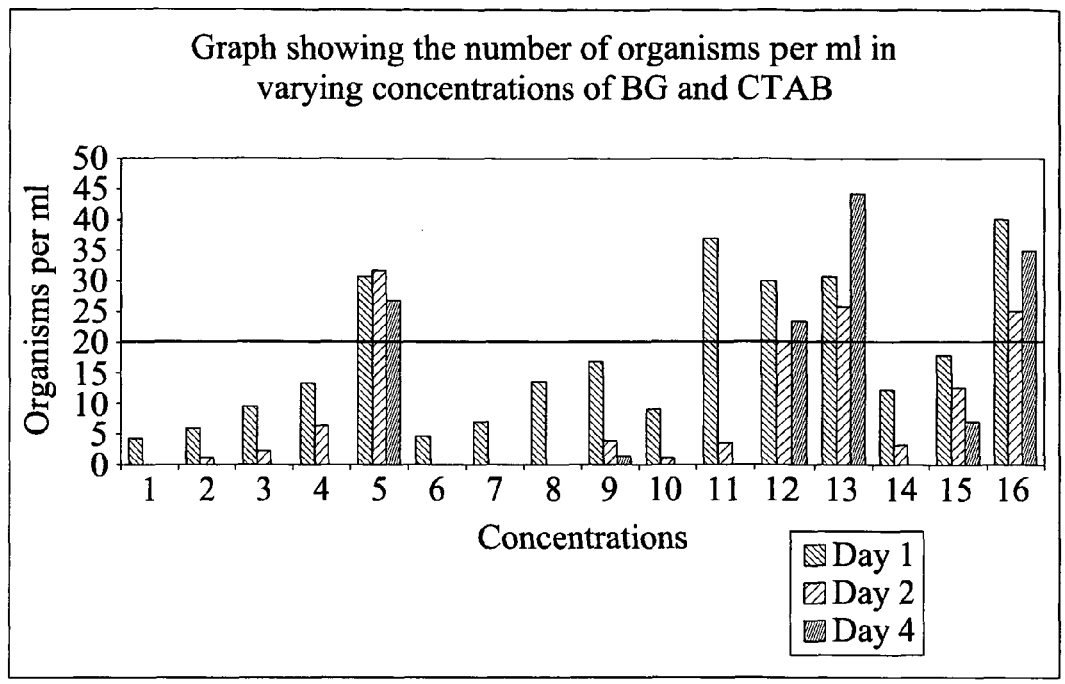
Fig 5.3
| Concentration Number | CTAB Concentration (mg/L) | BG Concentration (mg/L) |
|---|---|---|
| 1 | 1 | 0.5 |
| 2 | 0.8 | 0.4 |
| 3 | 0.6 | 0.3 |
| 6 | 1 | 0.1 |
| 7 | 0.8 | 0.2 |
| 10 | 0.5 | 0.5 |
Fig 5.4

| Concentration Number | CTAB Concentration (mg/L) | BG Concentration (mg/L) |
|---|---|---|
| 1 | 1 | 0.5 |
| 2 | 0.8 | 0.4 |
| 3 | 0.6 | 0.3 |
| 4 | 0.4 | 0.2 |
| 6 | 1 | 0.1 |
| 7 | 0.8 | 0.2 |
| 8 | 0.4 | 0.4 |
| 9 | 0.2 | 0.5 |
| 10 | 0.5 | 0.5 |
| 11 | 0.3 | 0.3 |
| 14 | 0.5 | 0.1 |

Fig 5.5

| Concentration Number | CTAB Concentration (mg/L) | BG Concentration (mg/L) |
|---|---|---|
| 1 | 1 | 0.5 |
| 2 | 0.8 | 0.4 |
| 3 | 0.6 | 0.3 |
| 4 | 0.4 | 0.2 |
| 6 | 1 | 0.1 |
| 7 | 0.8 | 0.2 |
| 8 | 0.4 | 0.4 |
| 9 | 0.2 | 0.5 |
| 10 | 0.5 | 0.5 |
| 11 | 0.3 | 0.3 |
| 14 | 0.5 | 0.1 |
| 15 | 0.2 | 0.4 |

Fig 5.6

| Concentration Number | CTAB Concentration (mg/L) | BG Concentration (mg/L) |
|---|---|---|
| 1 | 0.6 | 0.3 |
| 2 | 0.5 | 0.25 |
| 3 | 0.4 | 0.2 |
| 4 | 0.3 | 0.15 |
| 5 | CONTROL (0) | CONTROL (0) |

Fig 6.1

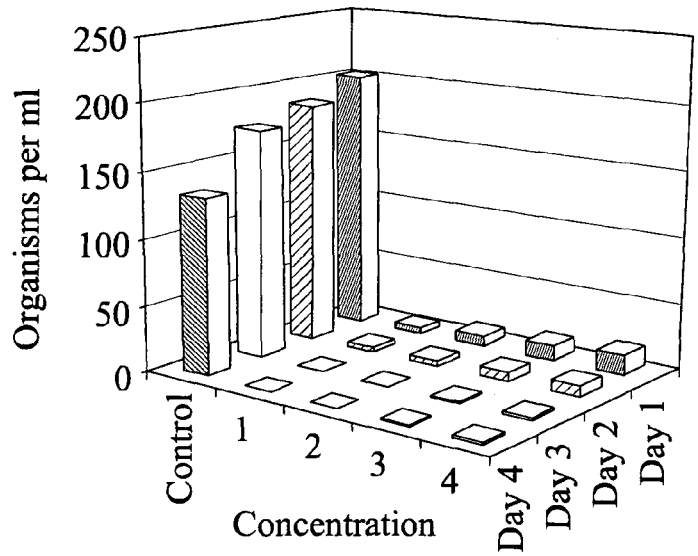
Fig 6.2
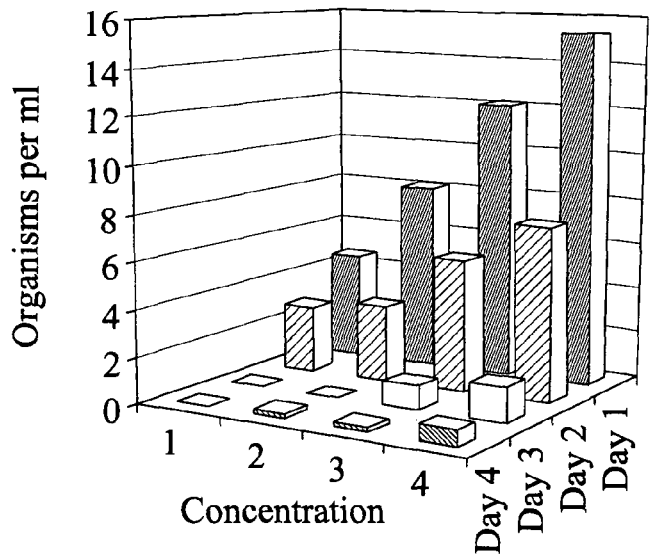
Fig 6.3

BALLAST WATER TREATMENT SYSTEM

FIELD OF INVENTION

The present invention relates to a system for treating waters, and in particular sea water in, e.g. a ship's ballast water tank, to prevent the introduction of non-indigenous marine species transferred by ships' ballast water, or in injection water for oil recovery to improve the recovery factor, prevent damage to the drilling equipment, and prevent contamination of the oil. In particular, though not exclusively, the present invention relates to a composition capable of killing unwanted marine species in a ship's ballast water tank or in injection water for oil recovery. The present invention also relates to an automated method and system for delivering, monitoring and/or controlling the dosing of the chemical formulation during treatment of ballast water. Finally, the present invention relates to a method of detecting viable aquatic organisms in ballast water in situ and, therefore, the efficacy of any treatment.

BACKGROUND TO INVENTION

Interest in identifying the most viable option for the treatment of biocontaminated ballast water has received worldwide recognition. It is estimated that approximately 3000 alien species are transported daily via ballast water making essential the need to deal with the aforementioned problem in the marine and coastal environments.

Allowing sea water ballast in certain compartments of the ship is the usual solution to compensate for lack of cargo loading in such a way that the operational characteristics of the ship are suitably adjusted. Accounting for movements of 7,000-10,000 species simultaneously and considering the vast amounts a typical commercial ship can carry, ballast water is the principal source of invasive species in coastal freshwater and marine ecosystems. Biological invasions are a leading cause of species extinctions and biotic homogenization worldwide. Ships' ballast water has been identified as an important vector for the introduction of non indigenous species, some of which may be responsible for significant negative commercial and health effects.

Problems associated with aquatic nuisance species have been estimated by the International Maritime Organization (IMO) to cost the global economy more than $100 billion annually, and have prompted the passage of the International Convention for the Control and Management of Ships' Ballast Water and Sediments in February 2004 that was modified by the 53rd Marine Environmental Protection Committee (MEPC 53) meeting in July 2005.

Many regulatory agencies and several state agencies have or are in the process of promulgating regulations governing methods of ballast water treatment (BWT) designed to eliminate the global transfer of alien species. Regulations have focused on two areas: approving specific technologies and discharge standards. The IMO published draft regulations including discharge standards that provide criteria for successful treatment. Discharge standards attempt to address both technical efficacy and enforcement practicality issues. However, it was clear from the published findings of MEPC 53 that technical difficulties remain in meeting these standards and the scope and detail of compliance monitoring remains a subject of debate.

One of the first guidelines recommended by the IMO was reballasting at sea and currently provides the best-available measure to reduce the risk of transfer of harmful aquatic organisms, but is subject to serious ship safety limits (due to instability issues). Even when it can be fully implemented, this technique is less than 100% effective in removing organisms from ballast water. Some parties even suggest that reballasting at sea may itself contribute to the wider dispersal of harmful species, and that island states located 'downstream' of mid-ocean reballasting areas may be at particular risk from this practice.

According to IMO, the criteria for alternative ballast water treatment technologies are:
 Safety for the ship and crew;
 Environmental impact (it must not cause greater impacts than it solves);
 Practicality (it must be compatible with ship design and operations);
 Cost; and
 Biological efficacy in terms of removing, killing or otherwise rendering inactive aquatic organisms and pathogens found in ballast water.

Various alternative methods to reballasting have been developed, including:
 Mechanical treatment methods such as filtration and physical separation;
 Physical treatment methods such as sterilisation by ozone, ultra-violet light, or electric currents; electro-ionisation; gas super-saturation; and heat treatment;
 Chemical treatment methods such adding oxidising or biocidal chemicals to kill organisms; and
 Various combinations of the above.

European Patent Application EP 1 717 205 A1 discloses removal of microbes to convert an untreated liquid to a clean harmless treated liquid, characterized in that the treatment of the liquid comprises a mechanical treatment for damaging microbes present in a liquid to effect extinction of the microbes and sterilization, combined with a chlorination in which a chlorine-containing substance is formed from a liquid and injected into a liquid to thereby effect microbe extinction and sterilization. There is further provided an electrolytic circulation system comprising applying a detoxification treatment for extinction of microbes in seawater and sterilization by means of detoxification facilities on land or on the sea to seawater introduced through a seawater introduction channel and accommodating the seawater having been thus treated in a ballast water tank. As a result, facility and operating costs can be reduced. Extinction of microbes of unlimited size and sterilization can be securely achieved without any strength drop on the side of treated liquid accommodation body. Further, the space for installation of detoxification apparatus for ballast water in ships can be reduced to thereby enable increasing of loading space for cargo, etc. Still further, on existing ships, the hull rework cost for installation of detoxification apparatus can be minimized.

US Patent Application No. US 2003 012 804 and PCT Patent Application No. WO 01/60971 disclose a method of controlling target aquatic microorganism pest populations by exposing the target population to an effective amount of an aquacidal compound. The aquacidal compounds are selected from the group consisting of quinones, anthraquinones, naphthalenediones, quinine, warfarin, coumarins, amphotalide, cyclohexadiene-1,4-dione, phenidione, pirdone, sodium rhodizonate, apirulosin and thymoquinone. The method is particularly effective for treating ballast water of ships or other enclosed volumes of water subject to transport between or among geographic areas to control the relocation of plants, toxic bacteria, and animals contained in the water.

US Patent Application No. US 2003 029 811 discloses systems and methods for effectively and economically annihilating non-indigenous marine species and pathogenic bacteria in ship ballast water. A preferred embodiment comprises adding a killing agent to ballast water tanks and subsequently adding a reducing agent to the container. Oxygen is subsequently introduced to the ballast water to eliminate any excess reducing agent, and to ensure compliance with the dissolved oxygen discharge requirements of the receiving water.

US Patent Application No. US 2003 129 645 discloses apparatuses and methods of a ballast water treatment system. The ballast water treatment system includes a control system and a ballast tank system. The control system controls the concentration of a biocide in the ballast tank system. In addition, the ballast water treatment system can be implemented in a vessel. The ballast water treatment system includes a control system, a biocide generation system, and a ballast tank system. The control system is capable of controlling the concentration of a biocide in the ballast tank system by controlling the amount of the biocide feed into the ballast tank system from the biocide generation system. Further, the ballast water treatment system involves methods for controlling organisms in ballast water of a vessel. A representative method includes providing the ballast water, and treating the ballast water with chlorine dioxide.

Another available chemical treatment for ballast water is the use of SeeKleen®. SeeKleen® is a commercial product marketed for use as natural biocide for ballast water treatment. Seakleen® is based on an antibiotic-medicinal, and more particularly menadione, also known as vitamin K3. Among the organisms claimed to be controlled are phytoplankton species, toxic dinoflagellates, dinoflagellates cysts, zebra mussel larvae, sheepshead minnow eggs and larvae, fathead minnow larvae, mysid shrimp larvae, grass shrimp larvae, copepods, spiny water flea, benthic amphipod protozoans and bacteria (*E. coli* and vibrio fisheri). However, experimental data show that while SeaKleen is very effective against zooplankton and other animal micro-organisms, it is thought to be less effective in killing plant organisms such as dinoflagellates or diatoms.

All the currently developed technologies have their limitations in application, in terms of efficacy, power consumption (operation cost), treatment flow rate, water turbidity and system corrosion, etc. More importantly, all the developed technologies have a limited treatment flow rate that is often less than the ballast and de-ballast rate of ship's normal operation that will delay the operation of ships. In addition, oxidation, de-oxygenation and ozone methods can cause corrosion problems to ship systems as well as posing a fire risk.

Therefore, there exists a need for a new technology that complies with IMO regulations, that is competitive in price, that is easy to install, operate onboard and maintain, that requires no major modification to the existing ballast systems, and that requires minimum training for crew to operate the system.

There also exists a need for an automated system and method for delivering, monitoring and controlling the dosing of the chemical formulation to ballast water.

Finally, there exists a need for a method of detecting viable micro-organisms in ballast water which is simple, reliable, fast, cost effective, and which does not require training of the operating crew or cumbersome equipment.

Treatment of water, and in particular sea water, is not only of interest in the field of ballast water. There exists other industrial applications in which the search for a composition capable of treating biocontaminated sea water has been the object of much research. One such application is the use of injection water for oil recovery.

During oil recovery from an oil well, the oil is initially driven to the surface by a number of natural mechanisms. This constitutes the primary recovery stage. These mechanisms include expansion of natural gas near the top of the reservoir, expansion of gas dissolved in the crude oil, gravity drainage within the reservoir and upward displacement of oil by natural water. However, the primary recovery stage typically provides a recovery factor of approximately 5-15% of the original oil.

When the underground pressure becomes insufficient to force the oil to the surface of the oil well, an increase in the recovery factor can be obtained by applying secondary recovery methods. These methods typically include gas injection and water injection. The use of secondary recovery techniques typically increases the recovery factor to approximately 15-40%.

A convenient source of fluid for injection is the produced water from the well. In an offshore environment, seawater is often the preferred source of injection water. Whichever source of water may be chosen, the purity of the water will affect the level of contaminants which are injected into the oil well. The presence of contaminants may cause 'plugging', i.e. the clogging of the well pores, which causes undesirable reduction of the recovery factor. The presence of contaminants may also cause scaling of the injection equipment. Additionally, the presence of bacteria such as sulphate reducing bacteria may cause 'souring' of the reservoir, i.e. contamination of the oil with hydrogen sulphide. Souring reduces the value of the produced hydrocarbons and requires expensive production equipment and materials to cope with the aggressive nature of the produced fluids.

Therefore, there exists a need for a composition capable of treating effectively injection water used in oil recovery.

It is an object of at least one embodiment of the present invention to seek to obviate or at least mitigate one or more disadvantages in the prior art.

It is an object of at least one embodiment of the present invention to provide a chemical composition capable of killing in situ aquatic invasive species in waters, typically sea water, and which is safe to be disposed of in the marine environment.

It is an object of at least one embodiment of at least one aspect of the present invention to provide an automated system for delivering, monitoring and controlling the dosing of the chemical composition to ballast water.

It is an object of at least one embodiment of at least one aspect of the present invention to provide a method of detecting micro-organisms in ballast water.

SUMMARY OF INVENTION

According to a first aspect of the present invention there is provided a composition for treating waters to kill in-situ aquatic invasive species, the composition comprising at least one biocide capable of killing both animal and plant micro-organisms.

The waters may comprise ballast water. In the context of the invention, ballast water is understood to mean water intended to be used to ballast any floating or semi-submersible structure having variable buoyancy such as ships, offshore platforms, e.g., semi-submersible oil platforms, or the like.

Alternatively, the waters may comprise injection water for oil recovery. Preferably, the injection water may comprise sea water.

Typically, the at least one biocide may comprise Brilliant Green, Gentian Violet, and/or erythrosine.

Typically, the concentration of each of the at least one biocide in the ballast water may be in the range of 0.01 to 5 mg/L, preferably in the range of 0.05 to 1 mg/L, more preferably in the range of 0.10 to 0.50 mg/L.

Typically, the concentration of each of the at least one biocide in the ballast water may be approximately 0.15 mg/L.

The composition may further comprise at least one herbicide. By such provision the composition may be more effective against both plant and animal micro-organisms.

Preferably, the at least one herbicide may comprise glyphosphate.

Conveniently, the composition may comprise at least 2 biocides that may show a synergistic effect in their biocidal activity.

The composition showing synergistic effect may comprise at least two of Brilliant Green, Gentian Violet, and/or erythrosine.

Conveniently, the at least one biocide in the composition may be substantially non-toxic to marine life upon post-treatment dilution into sea water.

The composition may further comprise at least one wetting agent or detergent-like compound. By such provision dispersion of the reagents of the composition in the ballast water may be ensured.

Typically, the ratio of the at least one wetting agent or detergent-like compound to the at least one biocide is in the range of 1:2 to 10:1, preferably in the range of 1:1 to 4:1.

Typically, the ratio of the at least one wetting agent or detergent-like compound to the at least one biocide is approximately 2:1.

Typically, the at least one wetting agent or detergent-like compound may comprise CTAB (cetyl trimethyl ammonium bromide) or CTAC (cetyl trimethyl ammonium chloride).

According to a second aspect of the present invention there is provided a system for treating ballast water in situ comprising means for injecting a composition for treating ballast water; means for measuring the flow rate or amount of ballast water to be treated; means for controlling the dosing of the composition; and means for storing or receiving the composition.

Conveniently, the means for injecting a composition for treating ballast water may be fitted or connected to at least one ballast water pump.

Preferably, the means for injecting a composition for treating ballast water may be fitted or connected to an inlet of the at least one ballast water pump. By such provision efficient mixing of the composition with the ballast water may be ensured.

Conveniently, the injection means may comprise at least one low-pressure injector.

Typically, the at least one low-pressure injector may have a pressure of 1 bar or lower.

Conveniently, the means for measuring the flow rate or amount of ballast water to be treated may be fitted or connected to at least one ballast water pump.

Preferably, the means for measuring the flow rate or amount of ballast water to be treated may be fitted or connected to an inlet of the at the least one ballast water pump.

Preferably, the means for measuring the flow rate or amount of ballast water to be treated may comprise at least one water flow meter.

Typically, the at least one water flow meter may be of the ultrasonic type.

In use, the at least one water flow meter may provide feedback to the control means.

In use, the control means may control the flow rate of the composition to the injection means.

Conveniently, the control means may adjust the flow rate of the composition to the injection means such that the concentration of the composition in the ballast water remains substantially constant.

Typically, the concentration of the composition in the ballast water may be maintained in the range of 0.01 to 5 mg/L, preferably in the range of 0.05 to 1 mg/L, more preferably in the range of 0.10 to 0.50 mg/L.

Typically, the concentration of the composition in the ballast water may be maintained in the region of 0.15 mg/L.

In use, the control means may be capable of recording at least one parameter of at least one component of the system during treatment of the ballast water.

Typically, the control means may be capable of recording at least one of the parameters selected from the list consisting of ballast water flow rate, dosing rate, and level of composition in storing means.

Preferably, the control means may be equipped with an alarm system to indicate the presence of at least one malfunction in the system.

Typically, the alarm system may be capable of indicating at least one malfunction selected from the list consisting of low level of composition in storing means, blockage of injection means, and power or circuitry defects.

The means for storing or receiving the composition may comprise a tank.

Conveniently, the size of the tank may be large enough to store an amount of composition sufficient for at least one complete treatment of ballast water.

Typically, the means for storing or receiving the composition may comprise a 15 L polypropylene tank.

Preferably, the storing means may be equipped with at least one means for indicating the level of composition inside of within the storing means.

The system may further comprise detection means for detecting the presence of viable micro-organisms in the ballast water.

Preferably, the detection means may comprise means for detecting metabolism in viable micro-organisms.

More preferably, the detection means may comprise means for detecting adenosine triphosphate (ATP) or adenosine diphosphate (ADP).

Most preferably, the detection means may comprise an ATP-based luminescence assay.

The detection means may have a detection limit in the region of $10\text{-}10^6$ cells or micro-organisms.

Typically, the detection means may have a detection limit in the region of $10^2\text{-}10^5$ cells or micro-organisms.

Conveniently, the detection means may be fitted or provided downstream from the at least one ballast water pump.

In use, the detection means may provide feedback to the control means.

Conveniently, the control means may adjust the flow rate of the composition to the injection means based on the signal provided by the detection means. By such provision the flow rate of the composition to the injection means may be, e.g.

reduced, if the detection means detects a substantially minimal or absent level of viable micro-organisms in the ballast water.

Conveniently, the control means may be at least party automated.

Preferably, the control means may comprise at least one computer or computer system.

According to a third aspect of the present invention there is provided a method of detecting in situ the presence of viable micro-organisms in ballast water.

Preferably, the method may comprise detecting metabolism in viable micro-organisms in ballast water.

More preferably, the method may comprise detecting the presence of adenosine triphosphate (ATP) in viable organisms in ballast water.

Most preferably, the method may comprise an ATP-based luminescence assay.

The detection method may have a detection limit in the region of $10$-$10^6$ cells or micro-organisms.

Typically, the detection method may have a detection limit in the region of $10^2$-$10^6$ cells or micro-organisms.

Preferably, the detection method may comprise concentrating a ballast water sample prior to detection.

Typically, the concentration step may comprise filtration or/and centrifugation of a ballast water sample.

Preferably, the detection method may further comprise lysing at least some of the micro-organisms prior to detection.

Typically, the lysis step may comprise adding a mixture comprising a detergent, e.g. CTAB (cetyl trimethyl ammonium bromide) or CTAC (cetyl trimethyl ammonium chloride), to a sample.

According to a fourth aspect of the present invention there is provided a method of treating ballast water in situ comprising delivering a biocidal composition to the water to be treated.

The method may further comprise the step of determining the amount of composition required to treat the ballast water.

Preferably, the step of determining the amount of composition required to treat the ballast water may comprise measuring the flow rate or amount of ballast water to be treated.

The method may further comprise the step of dosing the required amount of composition according to the flow rate or amount of ballast water to be treated.

Conveniently, the method may comprise automatically controlling the delivery of the composition to the ballast water.

Typically, the flow rate of ballast water may be measured at or near an inlet of a water ballast pump.

Typically also, the composition may be delivered or fed at or near an inlet of a water ballast pump. By such provision efficient mixing of the composition with the ballast water may be ensured.

Preferably, the method may further comprise detecting the presence of viable organisms in the ballast water. By such provision dosing of the composition can be adjusted when substantial elimination of viable organisms in the ballast water is achieved.

BRIEF DESCRIPTION OF DRAWINGS

Embodiments of the invention will now be given by way of example only, and with reference to the accompanying drawing, which are:

FIG. 2.1 a graph representing the correlation between bacterial cell numbers and bioluminescence in the case of *E. coli*;

FIG. 2.2 a graph representing the correlation between bacterial cell numbers and the bioluminescence in the case of *E. coli, represented in log units;*

FIG. 3.1 a graph representing ATP levels (measured using an ATP luminescence assay) in a sample of sea water against the number of days of incubation, when the sample was treated with various concentrations of Brilliant Green;

FIG. 3.2 a graph representing ATP levels (measured using an ATP luminescence assay) in a sample of sea water against the concentration of Gentian Violet added to the sample, with and without incubation;

FIG. 3.3 a graph representing ATP levels (measured using the ATP luminescence assay) in a sample of sea water against the concentration of erythrosine added to the sample, with overnight incubation, with and without light activation;

FIG. 3.4 a graph representing sulphur bacteria levels in a sample of sea water against the concentration of a composition consisting of 1:1 Brilliant Green/CTAB;

FIG. 4.1 a graph representing ATP levels (measured using the ATP luminescence assay) in a sample of sea water treated with Brilliant Green or Gentian Violet, against the number of days following treatment;

FIG. 4.2 a graph representing ATP levels (measured using the ATP luminescence assay) in a sample of sea water treated simultaneously with Brilliant Green and Gentian Violet, against the number of days following treatment;

FIG. 5.1 a table showing the various concentrations tested to acquire a set of working ratios and viable concentrations of CTAB and Brilliant Green in biocidal compositions according to a first embodiment of a first aspect of the invention;

FIG. 5.2 a graph representing the number of organisms per mL, against the concentrations of FIG. 5.1, measured over 4 days following treatment;

FIG. 5.3 the graph of FIG. 5.2, excluding measurement at Day 0 (i.e., immediately prior to treatment);

FIG. 5.4 a table showing a selection of working concentrations of CTAB and Brilliant Green in biocidal compositions effective at Day 1 subsequent to treatment;

FIG. 5.5 a table showing a selection of working concentrations of CTAB and Brilliant Green in biocidal compositions effective at Day 2 subsequent to treatment;

FIG. 5.6 a table showing a selection of working concentrations of CTAB and Brilliant Green in biocidal compositions effective at Day 4 subsequent to treatment;

FIG. 6.1 a table showing the various concentrations of CTAB and Brilliant Green in biocidal compositions selected to exhibit optimum efficacy;

FIG. 6.2 a graph representing the number of organisms per mL, against the concentrations of FIG. 6.1, measured over 4 days following treatment; and FIG. 6.3 the graph of FIG. 6.2, excluding control measurement.

DETAILED DESCRIPTION OF DRAWINGS

Figure 1:
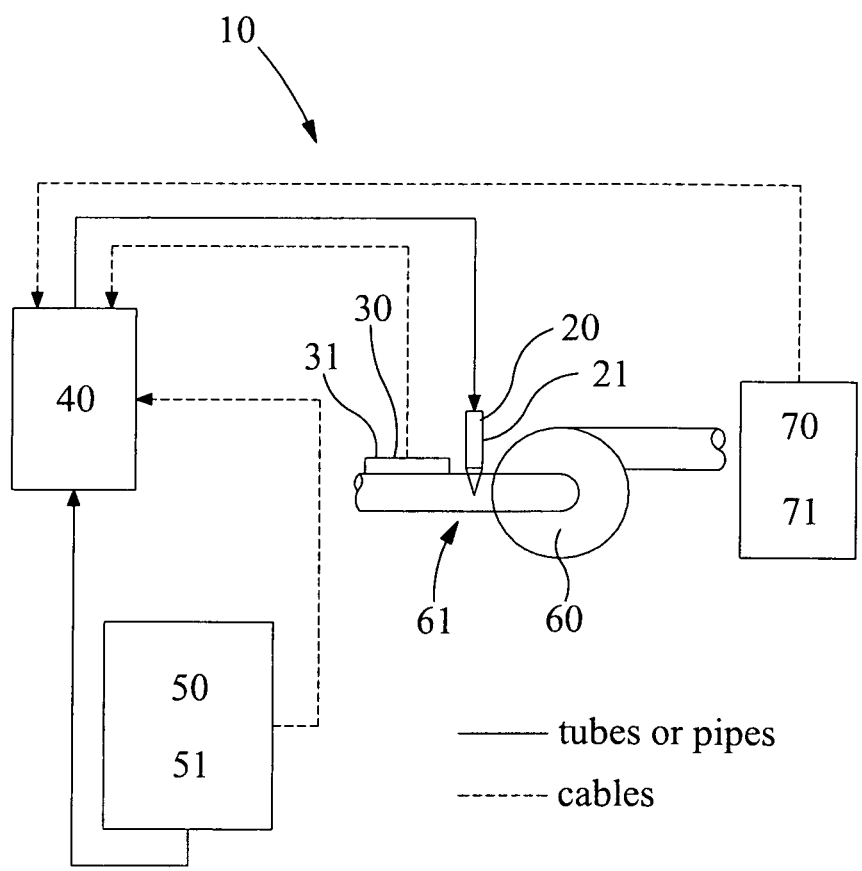
FIG. 1 a schematic representation of a ballast water treatment system according to a first embodiment of a second aspect of the present invention.

The first aspect of the present invention is directed to a composition for treating waters to kill in-situ unwanted marine animal and/or plant organisms, the composition comprising at least one biocide capable of killing both animal and plant micro-organisms.

In a first embodiment, the waters comprise ballast water. In the context of the invention, ballast water is understood to mean water intended to be used to ballast any floating or semi-submersible structure having variable buoyancy such as ships, off-shore platforms, e.g., semi-submersible oil platforms, or the like.

In an alternative embodiment, the waters comprise injection water for oil recovery, and more specifically sea water for offshore oil recovery.

In a preferred embodiment, the at least one biocide comprises at least one of Brilliant Green, Gentian Violet, and/or erythrosine. These compounds were generated at the beginning of the 20$^{th}$ Century and have been shown great efficacy as antibiotics for medical applications. In addition they are relatively inexpensive. These materials have been selected in the present invention for use in the treatment of ballast water.

Typically, the concentration of each of the at least one biocide in the ballast water is in the range of 0.01 to 5 mg/L, preferably in the range of 0.05 to 1 mg/L, more preferably in the range of 0.10 to 0.50 mg/L, and even more preferably approximately 0.15 mg/L.

In a preferred embodiment, the composition further comprises at least one herbicide. By such provision the composition is more effective against both plant and animal micro-organisms.

Preferably, the at least one herbicide comprises glyphosphate. The use of glyphosphate in the composition contributes to the elimination of marine animal organisms that possess plant-like metabolic pathways, e.g. dinoflagellates.

In a preferred embodiment, the composition comprises at least 2 biocides which show synergistic effect in their biocidal activity.

The composition showing synergistic effect comprises at least two of Brilliant Green, Gentian Violet, and/or erythrosine. The combined use of at least two of these compounds not only eliminates the growth of micro-organisms at extremely small concentrations but also shows synergistic biocidal effect to cover all classes of micro-organisms and prevent regrowth or bloom of a single species. This feature is particularly advantageous because any undesirable regrowth or bloom of unwanted marine species after release of treated ballast water can thus be avoided.

In this embodiment, the at least one biocide of the composition according to a first aspect of the present invention is substantially non-toxic to marine life upon post-treatment dilution into sea water. Typically, when diluted 2-3 fold from their typical working strength, these compounds are substantially non-toxic to all organisms.

In a preferred embodiment, the composition further comprises at least one wetting agent or detergent-like compound. By such provision dispersion of the reagents of the composition in the ballast water may be ensured.

In this embodiment, the at least one wetting agent or detergent-like compound comprises CTAB (cetyl trimethyl ammonium bromide). In addition to its dispersing properties, such a compound also has the advantage of possessing significant biocidal activity in its own right. It will be appreciated, however, that other wetting agents or detergents may be employed to the same effect.

Referring now to FIG. 1 there is shown a system for treating ballast water in situ, generally designated 10, according to a first embodiment of a second aspect the present invention. The system 10 comprises means for injecting 20 a composition for treating ballast water; means for measuring 30 the flow rate or amount of ballast water to be treated; means for controlling 40 the dosing of the composition, and means for storing or receiving 50 the composition.

Conveniently, the means for injecting 20 a composition for treating ballast water are fitted or connected to at least one ballast water pump 60.

In this embodiment, the means for injecting the composition are fitted or connected to an inlet 61 of the at least one ballast water pump 60. By such provision efficient mixing of the composition with the ballast water is ensured.

Conveniently, the injection means 20 comprises at least one low-pressure injector 21.

Typically, the at least one low-pressure injector 21 has a pressure of 1 bar or lower.

Conveniently, the means for measuring 30 the flow rate or amount of ballast water to be treated is fitted or connected to at least one ballast water pump 60.

In this embodiment, the means for measuring 30 the flow rate or amount of ballast water to be treated is fitted or connected to an inlet 61 of the at the least one ballast water pump 60.

In a preferred embodiment, the means for measuring 30 the flow rate or amount of ballast water to be treated comprises at least one water flow meter 31.

Typically, the at least one water flow meter 31 is of the ultrasonic type.

In use, the at least one water flow meter 31 is capable of providing feedback to the control means 40.

In use, the control means 40 controls the flow rate of the composition to the injection means 20.

Conveniently, the control means 40 adjusts the flow rate of the composition to the injection means 20 such that the concentration of the composition in the ballast water remains substantially constant.

Typically, the concentration of the composition in the ballast water is maintained in the range of 0.01 to 5 mg/L, preferably in the range of 0.05 to 1 mg/L, more preferably in the range of 0.10 to 0.50 mg/L.

More preferably, the concentration of the composition in the ballast water is maintained in the region of 0.15 mg/L.

In use, the control means 40 are capable of recording at least one parameter of at least one component of the system during treatment of the ballast water.

Typically, the control means 40 are capable of recording at least one of the parameters selected from the list consisting of ballast water flow rate, dosing rate, and level of composition in storing means 50.

In a preferred embodiment the control means 40 are equipped with an alarm system (not shown) to indicate the presence of at least one malfunction in the system.

Typically, the alarm system is capable of indicating at least one malfunction selected from the list consisting of low level of composition in storing means, blockage of injection means, and power or circuitry defects.

The means for storing or receiving 50 the composition comprise a tank 51.

Conveniently, the size of the tank 51 is large enough to store an amount of composition sufficient for at least one complete treatment of ballast water.

Typically, the storing means 50 comprises a 15 L polypropylene tank.

Conveniently, the storing means 50 is equipped with at least one means for indicating the level of composition inside of within the storing means.

In a preferred embodiment, the system 10 further comprises detection means 70 for detecting the presence of viable micro-organisms in the ballast water.

Preferably, the detection means 70 comprises means for detecting metabolism in viable micro-organisms.

More preferably, the detection means 70 comprises means for detecting adenosine triphosphate (ATP).

In this embodiment, the detection means comprises an ATP-based luminescence assay 71.

The detection means 70 has a detection limit in the region of $10-10^6$ cells or micro-organisms, and typically in the region of $10^2-10^5$ cells or micro-organisms.

Conveniently, the detection means 70 are fitted or provided downstream from the at least one ballast water pump 60.

In use, the detection means 70 is capable of providing feedback to the control means 40.

Conveniently, the control means 40 is capable of adjusting the flow rate of the composition to the injection means 20 based on the signal provided by the detection means 70. By such provision the flow rate of the composition to the injection means 20 may be, e.g. reduced, if the detection means 70 detects a substantially minimal or absent level of viable micro-organisms in the ballast water.

In a preferred embodiment, the control means is at least party automated, and comprises a computer or computer system.

The third aspect of the present invention is directed to a method of detecting in situ the presence of viable organisms in ballast water.

In a preferred embodiment, the method comprises detecting the presence of adenosine triphosphate (ATP) in viable organisms in ballast water.

In this embodiment, the method comprises an ATP-based luminescence assay. This established method is based upon the bioluminescent measurement of firefly luciferase. ATP is consumed and light is emitted when firefly luciferase catalyzes the oxidation of D-luciferin according to the following reaction:

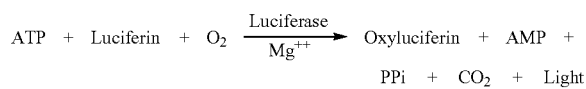

This reaction can be broken down into the following:

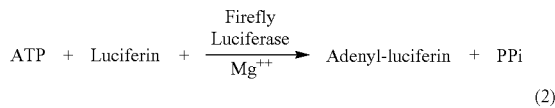

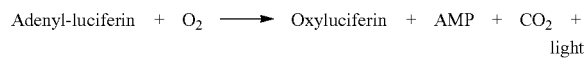

The ATP bioluminescent assay using firefly luciferase is a very sensitive, simple and rapid method of accurately determining levels of microbial ATP and therefore the number of bacteria present in a sample. An essential part of such assays is a cell lysis step that employs agents to release intracellular ATP. The released ATP is then measured using a bioluminescent reaction. The intensity of light emission is linearly related to the amount of microbial ATP and is measured using a luminometer. This method offers high sensitivity, consistent reproducibility and cost effectiveness. In addition, it offers the added convenience of a one step assay.

The detection method according to a third aspect of the present detection means has a detection limit in the region of $10-10^6$ cells or micro-organisms, and typically, in the region of $10^2-10^5$ cells or micro-organisms.

Preferably, the detection method comprises concentrating a ballast water sample prior to detection.

Typically, the concentration step comprises filtration or/and centrifugation of a ballast water sample.

Preferably, the detection method further comprises lysing at least some of the micro-organisms prior to detection.

Typically, the lysis step comprises adding a mixture comprising a detergent, e.g. CTAB (cetyl trimethyl ammonium bromide), to a sample.

Conveniently, the method can be carried out on site, rapidly, and can be performed by unskilled personnel.

It will be appreciated that minor variants of the present method may also be envisaged, e.g. ADP-based luminescence assay.

The fourth aspect of the present invention is directed to a method of treating ballast water in situ, which comprises delivering a biocidal composition to the water to be treated.

In a preferred embodiment, the method further comprises the step of determining the amount of composition required to treat the ballast water.

The step of determining the amount of composition required to treat the ballast water comprises measuring the flow rate or amount of ballast water to be treated.

In a preferred embodiment, the method comprises the step of dosing the required amount of composition according to the flow rate or amount of ballast water to be treated.

Conveniently, the method comprises automatically controlling the delivery of the composition to the ballast water.

Typically, the flow rate of ballast water is measured at or near an inlet of a water ballast pump.

Typically also, the composition is delivered or fed at or near an inlet of a water ballast pump. By such provision efficient mixing of the composition with the ballast water is ensured.

In a preferred embodiment, the method further comprises detecting the presence of viable organisms in the ballast water. By such provision dosing of the composition can be adjusted when substantial elimination of viable organisms in the ballast water is achieved. This helps minimise the amount of composition required to treat the ballast water, thus reducing cost and environmental impact.

It will be appreciated that the embodiments of the invention hereinbefore described are given by way of example only and are not meant to limit the scope thereof in any way.

It will particularly be appreciated that while the method of detecting in situ the presence of viable organisms in ballast water is preferably based on an ATP luminescence assay, minor variants thereof may also be employed, e.g. an ADP-based luminescence assay.

EXAMPLES

Methods and Materials

Sea samples were collected from Helensburgh (Scotland, UK) and the Largs area (Millport, Scotland, UK).

Initial screen of seawater sample prior to testing with various dyes revealed the following:

Zooplankton: Given the volume of water collected and sampled, low level of such was expected.

Phytoplankton: Samples for these can either be fixed in acidified Lugol's iodine or Formalin (10% solution). Alternatively, phytoplankton biomass can be assessed on basis of chlorophyll.

Bacteria: Method of direct involved using DAPI and counting under UV light. DAPI concentration used was 250 µg·mL$^{-1}$.

Reagents

The following materials were obtained from Sigma Chemical Co.:
  ATP assay mix: lyophilized powder containing luciferase, luciferin, MgSO$_4$, DTT, EDTA, BSA (bovine serum albumin), and tricine buffer salts;
  ATP Assay Mix Dilution Buffer: lyophilized powder containing MgSO$_4$, DTT, EDTA, BSA, and tricine buffer salts;
  Detergent solution: 1% (w/v) CTAB (cetyltrimethylammonium bromide) in nanopure water;
  ADP purified, Protease Inhibitors.

Preparation of Buffers

The contents of one vial of ATP Assay Mix were dissolved in 5 mL of sterile water to generate a stock solution with pH of 7.8. It was mixed by gentle inversion or swirling until dissolved. The solution was allowed to stand in ice for at least one hour to assure complete dissolution. The solution was divided into 0.1 mL aliquots in sterile micro-centrifuge tubes and stored at −20° C.

The contents of one vial of ATP Assay Dilution Buffer were dissolved in 50 mL of nanopure water. This solution was divided into 1 mL aliquots and stored at −20° C.

Assay—Preparation of Sample

Required quantities of each biocide dye were added to the tubes containing the sea sample by means of sterile pipettes in order to give the desired concentrations.

50 mL of each seawater sample was centrifuged at 4,000 rpm for 30 minutes at room temperature. The supernatant was discarded, and the pellets (which may not be visible) were resuspended in 1 mL of ATP Buffer Mix by brisk mixing with a sterile pastette. 0.1 mL of detergent solution was added to each sample. Sample tubes were then placed in a water bath at 90° C. for exactly 5 minutes to lyse seawater organisms. Alternatively the seawater organisms (from 50 mL water) are captured on a 0.22 µm filter membrane and treated with the ATP Buffer Mix, as above.

As a negative control, sterilised seawater (filtered through 0.22 µm filter and/or autoclaved) was used. Where coloured agents were added to the samples, these were also added to the negative control at the same concentration.

One aliquot (0.1 mL) of ATP Assay Mix solution was thawed and added to a sterile transparent 5 mL luminometer tube. This was swirled and allowed to stand at room temperature to allow hydrolysis of endogenous ATP and decrease background.

Immediately after 5 minutes of being at 90° C., 0.1 mL of resuspended seawater sample was added to the reaction tube, swirled briskly for 5 seconds, and immediately measured using a tube luminometer using a 4 second read time.

Correlation between Microbial Cell Number and Bioluminescent Signal

Bacterial strain Escherichia Coli was grown in Mueller Hinton II Broth at 37° C. overnight. The overnight culture was diluted 50-fold in fresh Broth and then incubated for several hours to reach log phase. Samples of the culture were serially diluted using Marine Broth in a 96-well plate.

Luciferase (Sigma) and luciferin (Sigma) were equilibrated for 1.5 hours at room temperature for improved sensitivity and added to each of the different culture samples. Luminescence was recorded on the luminometer and expressed in RLUs (relative light units). It will be appreciated that during reading, the first approximately 15,000 counts (RLU/s) are largely attributable to "background noise" and are therefore not relevant in the analysis of a sample.

The results of this analysis are shown in FIGS. 2.1 and 2.2. The graphs of FIGS. 2.1 and 2.2 depict the correlation between bacterial cell numbers and bioluminescence. Luminescent signals represent the mean of three replicates for each measurement. Bacterial cell numbers were determined by plate counting of colony forming units on agar plates. FIGS. 2.1 and 2.2 demonstrate a linear correlation between luminescent signal and the number of cells with a detection limit of approximately 10$^3$ bacterial cells.

Determination of the toxic effect of Brilliant Green, Gentian Violet, and Erythrosine in Sea Samples There are several possible ways of determining experimentally the bacteriostatic powers of various substances. Since primary interest concerns the ability of the biocidal substance to inhibit growth, the emphasis has been placed on bacteriostatic rather than bacteriocidal action. Bacteriostasis is probably simply a manifestation of vital staining, wherein the reproductive mechanism of the organism is destroyed or at least rendered inoperative.

Results

Measuring the lag phase in the presence of dye in relation to the normal lag phase in control organisms, FIG. 3.1 demonstrates that after incubation of sea samples from Millport for 13 days with 0.15 mg/L and 0.3 mg/L of Brilliant Green, there is a decrease in total ATP levels of the samples at second day. In addition there is a bloom of possible remaining bacteria observed at ninth day and then a final decrease in ATP levels after the twelfth day.

FIG. 3.2 shows the total ATP levels when treating sea samples from Millport with different concentrations of Gentian Violet, with and without incubation.

FIG. 3.3 shows the total ATP levels when treating sea samples from Millport with different concentrations of erythrosine, with overnight incubation, with and without light (60 w for 5 minutes).

FIGS. 3.2 and 3.3 show that both Gentian Violet and erythrosine possess effective biocidal properties in sea water.

Determination of the toxic effect of Brilliant Green in combination with CTAB on sulphur bacteria FIG. 3.4 shows the concentration of sulphur bacteria in a sample of sea water treated with different concentrations of a composition consisting of Brilliant Green and CTAB in a 1:1 ratio. As can be seen on FIG. 3.4, the treating composition shows effective biocidal properties in relation to sulphur bacteria, particularly in total concentrations of 0.3 mg/l and above.

Synergistic Effect

FIG. 4.1 shows the effect of Brilliant Green and Gentian Violet used separately on the viability of organisms in sea water. FIG. 4.1 illustrates the incomplete reduction in viability (as measured by ATP presence) and the bloom of a rod-like bacterium after 7-8 days.

FIG. 4.2 is a repeat experiment when Brilliant Green and Gentian Violet are used together. FIG. 4.2 shows complete elimination of the bloom and no detectable viable organisms at the end of the study period when the 2 reagents are used simultaneously. This was unexpected from the results shown in FIG. 4.1, and demonstrates the dramatic synergy in the biocidal effect of these two compounds.

Determination of Working Concentrations

In the process of formulating working concentrations of biocide dye and detergent in biocidal compositions, Brilliant Green was used as biocide, and CTAB was used as detergent.

The efficacy of various ratios of CTAB to Brilliant Green in the resulting biocidal compositions was then assessed using the method described above.

FIG. 5.1 shows the initial concentrations tested to acquire a set of working ratios and viable concentrations.

As shown in FIGS. 5.2 and 5.3, these concentrations showed various levels of efficacy in their biocidal effects.

The particular ratios and concentrations which displayed acceptable biocidal activity at day 1, day 2 and day 3 subsequent to treatment are shown respectively in FIGS. 5.4, 5.5, and 5.6. As shown in these tables, the best results were achieved for a range of ratios of CTAB to Brilliant Green of approximately 1:1 to 10:1, and for a range of Brilliant Green concentration of approximately 0.1 to 0.5 mg/L.

Efficacy Optimisation

Based of the results shown in FIGS. 5.2 and 5.3, and the working concentrations shown in FIGS. 5.4 to 5.6, optimised ratios and concentrations of CTAB and Brilliant Green were selected for use as a biocidal composition. These selected concentrations are shown in FIG. 6.1. In particular, a specific ratio of CTAB to Brilliant Green of 2:1 was selected, as well as concentrations of Brilliant Green in the range of 0.15 to 0.3 mg/L.

The biocidal effect of the concentrations of FIG. 6.1 was then tested again. The results are shown in FIGS. 6.2 and 6.3.

These results show that a ratio of CTAB to Brilliant Green of approximately 2:1 seemed to provide good efficacy in killing marine organisms. Further, concentrations of Brilliant Green in the range of 0.15 to 0.3 mg/L seemed to provide optimum results.

In use for the treatment of ballast water, it will be understood that selection of a particular concentration of biocidal dye may depend on the length of the sea voyage. For example, during a long voyage, a relatively low dose, such as concentration No. 4 of FIG. 6.1 (0.15 mg/L Brilliant Green), may be sufficient as the marine organisms are exposed to the biocidal composition over a relatively long time period. However, if the voyage is short e.g., 1 day, then a higher dose (such as concentration No. 1 of FIG. 6.1, 0.3 mg/L Brilliant Green) may be required to achieve a complete kill of aquatic nuisance species as exposure time is shorter.

It will be appreciated, however, that different ratios of CTAB to Brilliant Green may be effective depending on particular ballast water conditions. Further, different concentrations of Brilliant Green may also be effective depending on particular ballast water conditions.

Sea Trials

A seal trial was conducted upon Teekay Shipping's SS Polar Spirit commercial vessel. The SS Polar Spirit is a Liquid Natural Gas carrier conducting a 20 day round trip voyage from Yokohama Gas Terminal, Japan, to Nikiski Port, Ak. The total ballast water capacity of the vessel is 36570 m$^3$. Two round trips were arranged, allowing for 4 trials of the dosing system and efficiency of the treatment to be carried out.

Ballast water would only be taken on to the vessel after the discharge of the cargo, at Yokohama gas terminal, and would be subsequently discharged as cargo was loaded, at Nikiski Port. In order to maximise the number of trials carried out it was agreed that testing would be conducted on water contained in the ships stabiliser tanks during the return journey from Alaska to Japan, when all ballast water had been emptied. The ships stabiliser tanks would always be utilised for chemical treatment, due to the smaller volume which they contain and also the ability for them to be emptied during any stage of the voyage without interrupting the operational schedule. The larger ballast tanks would be kept for reference and control purposes. As the vessel would be carrying no ballast after the discharge of its cargo a stabiliser tank would have to be filled as a reference upon these legs of the journey.

The SS Polar Spirit was selected as the most beneficial vessel to conduct this trial aboard as the journey time of 9 days, port to port, provides a sufficiently long time scale for testing of lower concentrations, slower effectiveness treatments and also travels between 2 environmentally different bodies of water. In contrast to the fully marine water encountered in the discharge port of Yokohama, the water at the cargo loading port of Nikiski, Ak., is brackish in nature due to considerable input from fresh water streams and glacial melt water, into the bay area. Thus, the 2 port areas offer a wider variety of species of aquatic organisms and environmental parameters than would be found from a vessel travelling solely in marine waters. Therefore, the system was subjected to a diverse range of water temperatures, sediment loadings, salinities and species during the trials.

The dosing unit and chemicals, comprising the treatment method, were shipped and installed on board the vessel along with the necessary scientific research equipment, prior to the arrival and embarkation of the research personnel, by arrangement from Teekay Shipping. The dosing unit was installed by the ships engineers to dispense the chemical treatment into Ballast Pump number 1. The dosing unit was fitted with 2×60 liter solution tanks in which the treatment solution was prepared from the powdered chemicals.

For these sea trials, the treatment compositions used consisted of a mixture of BG (Brilliant Green) and CTAB (cetyl trimethyl ammonium bromide) at a ratio of 1:2, and in various concentrations. This formulation was given the name "ClearBal".

Sea Trial Number 1: Narita Port, Chiba, Japan, to Nikiski Port, Ak.

Introduction:

As the ship discharged its cargo it would draw in sea water ballast in order maintain its stability and trim for the voyage to Alaska. A stabiliser tank was filled with 500 m$^3$ of water for the purpose of testing the first chemical concentration whilst ballast tank number 3 was used as a reference tank, containing 3927 m$^3$ of water. Both tanks were filled with water from the Narita Port area, Chiba.

For this first trial a concentration 0.9 mg/l ClearBal treatment, comprised of 0.6 mg/l CTAB (cetyl trimethyl ammonium bromide) and 0.3 mg/l BG (Brilliant Green) were investigated. This concentration was the desired final concentration to employ, in the system, as it was found (in the laboratory) to be the lowest concentration of chemical agents which produced the desired outcomes in a short time frame.

Method:

For the 500 m$^3$ of water to be treated it was necessary for 9 liters of a 5% solution of the ClearBal treatment to be added via the dosing unit through the ballast pump. 500 g of CTAB and 250 g of BG were weighed and dissolved in 15 liters water in the storage tank. The pipe work was primed with the dosing solution prior to administration to the selected tank.

Biological and efficacy tests were carried out by taking a reference sample of untreated water, from the ballast system, to give a day 0 figure for biological content, then sampling both reference and treated tanks at time intervals.

Day 0 sampling was accomplished by diverting water from the incoming ballast pumps to the fire hose system. By using a fire hose 5 m$^3$ was passed through a 50 μm mesh filter and the retained organisms extracted for analysis and counting. This process would only allow assessment of organisms greater than 50 μm. The IMO guidelines for ballast water quality require that organisms over 50 μm are assessed and also organisms less than 50 μm but over 10 μm be assessed. In order to achieve this it was necessary to take a further 20 liters of water directly from the ballast tank with no filtering. In this instance the vessels were filled using the fire hose.

Subsequent samples of water were taken at 36, 52, 58 and 76 hour intervals from time 0. In order to prevent damaging of marine species from the sampling, these samples were taken by vertically drawing a 50 μm plankton tow net through the water in the tanks under investigation. By calculating the area of the opening of the net and multiplying this by the vertical distance drawn through the water, the volume of water which has passed through the net can be obtained. This method gently retains the species over 50 μm and there is less chance of false results due to organisms being killed in the sampling process. To extract water for analysis of organisms less than 50 μm but greater than 10 μm, Niskin water bottles were used to extract 5 liters of water at a time, from 3 different vertical depths in the tanks. These were the top, middle and bottom of the water column. The access to the water in the tanks was via the manholes situated on the deck.

Environmental parameters were assessed by measuring the salinity, temperature, pH and dissolved oxygen content of the water using hand held measuring devices immediately after extraction of the samples.

The biological content of the samples was assessed using microscopy. The water samples were analysed using Sedgewick Rafter counting chambers which allow representative counting of the species present. The chambers hold 1 ml of liquid, and are divided into a 1000 squares which are visible under the microscope. By counting organisms in a number of squares and then scaling the figure obtained up by a value, calculated by 1000 divided by the number of squares counted, an accurate indication of the number of organisms present in the 1 ml can be obtained. As the volume of water which had passed through the plankton tow net was known, it could be assumed that the organisms retained in the net were the total number of organisms from that volume of water. These organisms were then suspended in 100 ml seawater, by analysing species present in 100, 1 ml counting chambers the whole 100 ml of concentrate could be accurately counted and this number would be the number of organisms present in the total volume of water which had passed through the tow net. This allowed an assessment of the treatment in its ability to meet the IMO ballast water quality guideline of no more than 10 organisms greater than 50 μm in 1 m$^3$ of water.

Organisms less than 50 μm but greater than 10 μm were not concentrated by a filter, like organisms greater than 50 μm, but were assessed in a similar manner, using the counting chambers. The IMO guideline states that treated ballast water must contain no more than 10 of these individuals per 1 ml of water. From the 15 liters of water extracted for analysis of this size range, 100 ml was counted in the 1 ml counting chambers.

Results:
Species greater than 50 μm in size:
0 hour species numbers: 9066 per m$^3$

TABLE 1

Table 1: Number of Organisms per m$^3$ which are greater than 50 μm:

| Treatment Time | Number of Organisms > 50 μm | |
|---|---|---|
| (hrs) | Control | 0.9 mg/l ClearBal |
| 38 | 7886.54 | 392.35 |
| 54 | 7420.63 | 77.34 |
| 60 | 6849.09 | 37.73 |
| 78 | 5817.29 | 9.43 |

Table 1 shows the number of organisms greater than 50 μm present in both the tank treated with ClearBal and the reference tank. From an initial figure of 9066 organisms per m$^3$ it can be seen that there is some reduction in the control tank but within 78 hrs the tank treated with ClearBal solution has reached a figure of 9.43 organisms per m$^3$ and therefore is inside the IMO ballast water condition guideline. At the same time interval the reference tank contains 5817.29 organisms per m$^3$.

Species less than 50 μm but greater than 10 μm in size:
0 hour species numbers: 112 per ml

TABLE 2

Table 2: Number of Organisms per ml which are less than 50 μm but greater than 10 μm,

| Treatment Time | Number of Organisms < 50 μm | |
|---|---|---|
| (hrs) | Control | 0.9 mg/l ClearBal |
| 38 | 75.50 | 0 |
| 54 | 385 | 0 |
| 60 | 60 | 0 |
| 78 | 214 | 0 |

Table 2 shows the number organisms per ml which are less than 50 μm but greater than 10 μm in size present in the tank treated with ClearBal and the reference tank. It can be seen that from an initial figure of 112 organisms per ml of water the ClearBal treatment has reduced this figure to 0 within 38 hours. This meets the IMO guideline of less than 10 organisms per ml of ballast water. The control numbers do fluctuate but are considerably higher than those of the treated tank.

Environmental Parameters:
Environmental parameters were measured, including pH, temperature, salinity, and dissolved oxygen. Very little change was observed over the dureation of the experiment. This was the same for both tanks, treated and untreated.

Conclusions:
The 0.9 mg/l concentration of ClearBal treatment, comprised of 0.6 mg/l CTAB and 0.3 mg/l BG, was able to successfully condition the ballast water in the treated tank to a standard acceptable under the IMO guidelines. The effective treatment time was found to be approximately 78 hours. Furthermore, the organism numbers in the untreated reference tank remained at a very high level, indicating that the ClearBal treatment is responsible for the decline in species numbers. Reductions in species numbers in the reference tank could be attributed to a natural decline due to the disruption of passing through the ballasting system and the deprivation of daylight. However, from an initial figure of 9066 organisms per m³ the reference tank still contained 5817 organisms per m³, at the 78 hour interval, when the treated tank contained 9 organisms per m³.

The treatment was shown to be effective against a wide range of Zooplankton and Phytoplankton species, Crustaceans, Molluscs, Bi-valves, Polychaetes, Radularians, Flagellates and Diatoms, all of which were observed in the ballast water. This demonstrates that the ClearBal treatment is effective against a wide range of species.

Sea Trial Number 2: Nikiski Port, Ak., to Yokohama Gas Terminal, Japan

Introduction:

The second sea trial of the ClearBal system was carried out during the voyage from Nikiski Port, Ak., to Yokohama Gas Terminal, Japan. A 0.6 mg/l concentration of ClearBal treatment was used, comprised of 0.4 mg/l CTAB and 0.2 mg/l BG. The intention of this trial was to use a lower concentration of the treatment but allow for a longer time period for effectiveness.

As the vessel was devoid of ballast water for the return journey to Japan, the trial used 2 stabiliser tanks, to serve as reference and treated. The amount of water contained in the reference and treated tanks was 500 m³ and 338 m³ respectively.

Method:

Sampling of the 0 hour and subsequent time intervals of 60, 85, 110, 135, 160 and 185 hours was carried out by accessing the stabiliser tanks through deck manholes. The vertical hauling of a 300 mm diameter 50 µm plankton tow through a known water depth was used to extract organisms greater than 50 µm in size and Niskin water sampling bottles used to extract water to be examined for organisms less than 50 µm but greater than 10 µm in size. Environmental parameters, of the extracted water, would be carried out in the same manner as previously employed; using hand held instrumentation and the analysis of the biological content of the water carried out via microscopy and counting chambers.

Results:

Species Greater than 50 µm in Size:

TABLE 3

Table 3: Number of Organisms per m³ which are greater than 50 µm

| Treatment Time | Number of Organisms > 50 µm | |
|---|---|---|
| (hrs) | Control | 0.6 mg/l ClearBal |
| 60 | 301.45 | 78.11 |
| 85 | 261.67 | 61.15 |
| 110 | 216.20 | 42.95 |
| 135 | 121.57 | 30.30 |
| 160 | 99.82 | 14.87 |
| 185 | 57.82 | 9.17 |

Table 3 shows the number of organisms greater than 50 µm in size contained in treated and reference tanks. It can be seen that by the 185 hour interval that the 0.6 mg/l has reduced the number of organisms to a level acceptable under the IMO guidelines for ballast water quality. The numbers in the control tank do steadily fall between the 60-185 hour time intervals, but still remain far higher than those observed in the treated tanks throughout sampling.

Species Less than 50 µm but Greater than 10 µm in Size:

TABLE 4

Table 4: Number of Organisms per ml which are less than 50 µm

| Treatment Time | Number of Organisms < 50 µm | |
|---|---|---|
| (hrs) | Control | 0.6 mg/l ClearBal |
| 60 | 35 | 0 |
| 85 | 15 | 1 |
| 110 | 28 | 0 |
| 135 | 23 | 0 |
| 160 | 19 | 0 |
| 185 | 12 | 0 |

Table 4 shows the number of organisms per ml which are less than 50 µm but greater than 10 µm in size present in the tank treated with ClearBal and the reference tank. It can be seen that by the 60 hour time interval the 0.6 mg/l of ClearBal treatment has reduced the number of organisms to a level acceptable under the IMO ballast water guidelines. As with the organism greater than 50 µm in size the reference numbers do drop over 185 hour time period but are far higher than those in the treated tank.

Environmental Parameters:

Over the 185 hour measurement period little variation was observed in terms of temperature, salinity, pH and dissolved oxygen, in both tanks.

Conclusions:

The 0.6 mg/l concentration of ClearBal solution, comprising 0.4 mg/l CTAB and 0.2 mg/l BG, was able to condition the water to meeting IMO standards in a time period of 185 hours. This concentration was anticipated as requiring a longer time frame in which to be effective. The 185 hours required, which was higher than the 96 hours observed during laboratory experiments, may have been due to a number of factors. Noticeable during the analysis of the water samples was that there was a specific diatom which continued to survive in the treated water when all other species had died. This diatom was the sole component of the organisms found in the treated water after 110 hours. This species appears to be very hardy and resistant to the effects of the treatment. The brackish water, found in the Nikiski Bay area, presents a very hard environment for survival, due to the regular changing from saltwater to fresh water, and organisms develop mechanisms to overcome this. The other species observed did succumb to the effect of the treatment at the 110 hour point. The mount of sediment in the water may also have had an effect on the efficacy of the treatment.

Species diversity in the Nikiski Bay water was far less than that encountered in Narita Port, for environmental reasons previously mentioned. Observed during this trial were only Diatom and Crustacean species.

This second trial confirmed that sediments will affect the action of the treatment, with potential for different sediments to have differing degrees of effect. Also observed has been that some species can be more resistant to the effect of the treatment than others.

Sea Trial Number 3: Yokohama Gas terminal, Japan, to Nikiski Port, Ak.

Introduction:

For this journey 2 treatments with high concentrations and short effectiveness were be tested. The concentrations of ClearBal to be used were 1.2 mg/l comprised of 0.8 mg/l CTAB and 0.4 mg/l BG, and 1.5 mg/l, comprised of 1 mg/l CTAB and 0.5 mg/l BG. These concentrations of treatment were found to be effective within 24 hours during the laboratory based investigations.

As 2 concentrations were under investigation during this trial, the fore and aft stabiliser tanks would be used for experimenting with the treatment, and ballast tank number 3 utilised as a reference tank. The aft stabiliser was used to test the 1.5 mg/l solution and contained 554 m³ of water and the fore stabiliser was used to test the 1.2 mg/l concentration and contained 333 m³ of water.

Method:

The sampling was also carried out as previously described using a 300 mm 30 μm tow net and Niskin sampling bottles. Hand held instrumentation was used to record environmental parameters and the biological content of the water assessed using microscopy and counting chambers.

Results:
Species Greater than 50 μm in Size:

TABLE 5

Table 5: Number of Organisms per m³ which are greater than 50 μm

| Treatment Time (hrs) | Number of Organisms > 50 μm | | |
|---|---|---|---|
| | Control | 1.2 mg/l ClearBal | 1.5 mg/l ClearBal |
| 39 | 678070.84 | 176.84 | 0 |
| 62 | 565607.98 | 0 | 0 |

Table 5 shows the effectiveness of the 1.2 mg/l and 1.5 mg/l solutions of ClearBal. The 1.5 mg/l solution has conditioned the water to IMO standards by the 39 hour period and the 1.2 mg/l solution has achieved the effect after a 62 hour period. During this period the number or organisms present in the reference tank remain high, at the 62 hour period being 565607 per m³ compared to 0 for the treated water.

Species Less than 50 μm but Greater than 10 μm in Size:

TABLE 6

Table 6: Number of Organisms per ml which are less than 50 μm, in ballast water containing 1.2 mg/l and 1.5 mg/l ClearBal

| Treatment Time (hrs) | Number of Organisms < 50 μm | | |
|---|---|---|---|
| | Control | 1.2 mg/l ClearBal | 1.5 mg/l ClearBal |
| 39 | 886 | 0 | 0 |
| 62 | 267 | 0 | 0 |

Table 6 shows the number of organisms less than 50 μm but greater than 10 μm in size found in the treated and reference water, per m³. Both the 1.5 mg/l and 1.2 mg/l solutions conditioned the water to meet IMO standards for species in this size range, by the 39 hour period. For the 39 and 62 hour intervals the untreated reference water contains considerably higher species numbers.

Environmental Parameters:

Across the 62 hour time period of this investigation the environmental parameters present in the stabiliser tanks and the reference tank were found to be very comparable and to vary little, during the time period.

Conclusions:

The 1.5 mg/l and 1.2 mg/l solutions of ClearBal were able to condition the water to meet IMO regulations at 39 hours, for 1.5 mg/l, and 62 hours, for 1.2 mg/l.

A wide range of species were present in the water from Yokohama. This demonstrates the ability of the ClearBal treatment to be effective against a wide range of species. Observed were small fish, jelly fish, lobster larvae, crab larvae, mollusc and bi-valve larvae and many different phytoplankton species.

The treatment was successful in conditioning the treated water to meet IMO ballast water guidelines. Species abundance and diversity does not seem to be an issue as, particularly from Japanese waters, far greater numbers and types of species are present in the ballast water than that which was used during the laboratory based experiments.

Sea Trial Number 4: Nikiski Port, Ak., to Yokohama Gas Terminal, Japan

Introduction:

A test using a further increase of treatment concentration was carried out. The water and organisms from Nikiski bay had previously been very resilient to a lower dosage of treatment and so a concentration of 1.8 mg/l ClearBal, comprised of 1.2 mg/l CTAB and 0.6 mg/l BG, was used.

As for sea trial number 2, the stabiliser tanks would act as one for reference and one for treated. The reference tanks contained 554 m³ of water and the treated stabiliser tank 333 m³ of water.

Method:

The sampling was carried out as previously described using a 300 mm 30 μm tow net and Niskin sampling bottles. Hand held instrumentation was used to record environmental parameters and the biological content of the water assessed using microscopy and counting chambers. Samples were taken at the 24, 64, 89, 114 and 139 hours time intervals with access to the tanks under investigation being gained through the deck manholes.

Results:
Species Greater than 50 μm in Size:

TABLE 7

Table 7: Number of Organisms per m³ which are greater than 50 μm

| Treatment Time (hrs) | Number of Organisms > 50 μm | |
|---|---|---|
| | Control | 1.8 mg/l ClearBal |
| 24 | 99854.99 | 11423.79 |
| 64 | 86297.35 | 18120.09 |
| 89 | 81110.08 | 6778.82 |
| 114 | 68259.79 | 683.78 |
| 139 | 48218.05 | 0 |

Table 7 shows the effect of 1.8 mg/l of ClearBal treatment at 24, 64, 89, 114 and 139 hours. It can be seen that the concentration is effective at the 139 hour point. The number of organisms per m³ decreases slowly over the 24-89 hour time period and falls sharply in from 89-139 hours. The organisms in the reference tank do show a reduction in numbers, over the 24-139 hour time period, but numbers per m³ are still considerably higher than the treated tank.

Species Less than 50 μm but Greater than 10 μm in Size:

TABLE 8

Table 8: Number of Organisms per ml which are less than 50 μm

| Treatment Time (hrs) | Number of Organisms < 50 μm | |
|---|---|---|
| | Control | 1.8 mg/l ClearBal |
| 24 | 40 | 0 |
| 64 | 16 | 0 |
| 89 | 4 | 0 |

TABLE 8-continued

Table 8: Number of Organisms per ml which are less than 50 μm

| Treatment Time (hrs) | Number of Organisms < 50 μm | |
|---|---|---|
| | Control | 1.8 mg/l ClearBal |
| 114 | 0 | 0 |
| 139 | 0 | 0 |

Table 8 shows the number of organisms less than 50 μm but greater than 10 μm in size contained within the reference and treated tanks. The ClearBal treatment has removed all organisms, within this size range, at the 24 hour period. Numbers within the reference tank remain high for the first 64 hours but are severely reduced by the 89 hour period and not observed at the 114 and 139 hour period.

Environmental Parameters:

The environmental parameters, namely the temperature, salinity, pH and dissolved oxygen were very comparable in the 2 tanks and varied little across the 139 hour time period.

Conclusions:

The 1.8 mg/l solution of ClearBal, comprised of 1.2 mg/l CTAB and 0.6 mg/l BG, was able to condition the water to IMO discharge standards after 139 hours. This relatively long time may be accounted for by the observations which were previously recorded during Sea Trial 2. It had been observed that quantity and type of sediment, suspended in the water, seemed to have a negative effect upon the effectiveness of the treatment. It is believed that the glacial sediments from Alaska have an ability to neutralise the active components of the treatment far more efficiently than the marine sediments found in Japanese water. Further to this a very resilient species of Diatom was encountered in the Alaskan brackish waters that required considerable exposure to the treatment to be killed. This species was present in abundant numbers during this fourth trial. All other organisms were killed by the 64 hour point. From the results obtained for species less than 50 μm but greater than 10 μm in size it can be seen that the treatment was effective after 39 hours. These smaller flagellate species, like the other phytoplankton species from the Alaskan waters, did not have the ability to resist the effects of the treatment and so were killed in a short time period.

General Conclusion

The ClearBal treatment has been found to be successful in conditioning ballast water to the standards required by the IMO guidelines. Various concentrations have been found to be effective over various time scales. The dosing unit and manufacture of chemical solution, from powdered components, was found to be a simple and efficient process which could easily be carried out in the industrial environment of commercial shipping.

The invention claimed is:

1. A composition for treating waters to kill in-situ aquatic invasive species, the composition comprising at least one biocide capable of killing both animal and plant micro-organisms, wherein the at least one biocide comprises Brilliant Green and/or Gentian Violet,
the composition further comprising at least one wetting agent or detergent-like compound, wherein the at least one wetting agent or detergent-like compound comprises CTAB (cetyl trimethyl ammonium bromide) or CTAC (cetyl trimethyl ammonium chloride),
wherein the weight ratio of the at least one wetting agent or detergent-like compound to the at least one biocide is in the range of 1:2 to 10:1, and wherein the composition does not include a herbicide.

2. The composition according to claim 1, wherein the concentration of each of the at least one biocide in the waters is in the range of 0.01 to 5 mg/L.

3. The composition according to claim 1 wherein the concentration of each of the at least one biocide in the waters is in the range of 0.10 to 0.50 mg/L.

4. The composition according to claim 1 wherein the concentration of each of the at least one biocide in the waters is approximately 0.15 mg/L.

5. The composition according to claim 1, wherein the composition comprises at least 2 biocides that show a synergistic effect in their biocidal activity, wherein the at least 2 biocides comprises Brilliant Green and Gentian Violet.

6. The composition according to claim 1, wherein the at least one biocide in the composition is substantially non-toxic to marine life upon post-treatment dilution into sea water.

7. The composition of claim 1, wherein the weight ratio of the at least one wetting agent or detergent-like compound to the at least one biocide is approximately 2:1.

8. The composition according to claim 1, wherein the waters comprise ballast water.

9. The composition according to claim 1, wherein the waters comprise injection water for oil recovery.

10. A method of treating ballast water in situ comprising delivering to the water to be treated a biocidal composition,
the composition comprising at least one biocide capable of killing both animal and plant micro-organisms, wherein the at least one biocide comprises Brilliant Green and/or Gentian Violet,
the composition further comprising at least one wetting agent or detergent-like compound, wherein the at least one wetting agent or detergent-like compound comprises CTAB (cetyl trimethyl ammonium bromide) or CTAC (cetyl trimethyl ammonium chloride),
wherein the weight ratio of the at least one wetting agent or detergent-like compound to the at least one biocide is in the range of 1:2 to 10:1, and wherein the composition does not include a herbicide.

11. The method according to claim 10, further comprising the step of determining the amount of composition required to treat the ballast water.

12. The method according to claim 11, wherein the step of determining the amount of composition required to treat the ballast water comprises measuring the flow rate or amount of ballast water to be treated.

13. The method according to claim 12, wherein the flow rate of ballast water is measured at or near an inlet of a ballast water pump.

14. The method according to claim 10, wherein the method further comprises the step of dosing the required amount of composition according to the flow rate or amount of ballast water to be treated.

15. The method according to claim 10, wherein the method comprises automatically controlling the delivery of the composition to the ballast water.

16. The method according to claim 10, wherein the composition is delivered or fed at or near an inlet of a ballast water pump.

17. The method according to claim 10, wherein the method further comprises detecting the presence of viable organisms in the ballast water.

* * * * *